United States Patent
Mutel et al.

(10) Patent No.: US 10,813,962 B2
(45) Date of Patent: Oct. 27, 2020

(54) SAXIFRAGA EXTRACTS FOR COSMETIC OR THERAPEUTIC USE ON THE SKIN

(71) Applicant: TauDerma SA, Conthey (CH)

(72) Inventors: Vincent Mutel, Rolle (CH); Xavier Simonnet, Fully (CH); Bruno Schnyder, Crans (CH)

(73) Assignee: TauDerma SA, Conthey (CH)

( * ) Notice: Subject to any disclaimer, the term of this patent is extended or adjusted under 35 U.S.C. 154(b) by 103 days.

(21) Appl. No.: 16/096,241

(22) PCT Filed: May 3, 2017

(86) PCT No.: PCT/IB2017/052579
§ 371 (c)(1),
(2) Date: Oct. 24, 2018

(87) PCT Pub. No.: WO2017/191581
PCT Pub. Date: Nov. 9, 2017

(65) Prior Publication Data
US 2019/0160124 A1    May 30, 2019

Related U.S. Application Data

(60) Provisional application No. 62/331,236, filed on May 3, 2016, provisional application No. 62/356,327, filed on Jun. 29, 2016.

(51) Int. Cl.
*A61K 36/185* (2006.01)
*A61Q 19/08* (2006.01)
(Continued)

(52) U.S. Cl.
CPC .......... *A61K 36/185* (2013.01); *A61K 8/9789* (2017.08); *A61K 9/06* (2013.01);
(Continued)

(58) Field of Classification Search
CPC .................................................. A61K 36/185
See application file for complete search history.

(56) References Cited

U.S. PATENT DOCUMENTS

| | | | |
|---|---|---|---|
| 6,406,682 B1 * | 6/2002 | Martin | A61K 8/97 424/400 |
| 2004/0161478 A1 * | 8/2004 | Nakagiri | A23K 20/10 424/725 |
| 2015/0050316 A1 | 2/2015 | Stangl | |

FOREIGN PATENT DOCUMENTS

| | | |
|---|---|---|
| EP | 1536811 | 6/2005 |
| EP | 2229940 | 9/2010 |

(Continued)

OTHER PUBLICATIONS

Bastian et al. 2009 "*Saxifraga rotundiofolia* L.: détermination du stade de récolte en fonction de la phénologie et de la phytochimie." (Revue Suisse Vitic. Arboric. Hortic. (2009), 41 (6),363-367) (translation and original article).

(Continued)

*Primary Examiner* — Rosanne Kosson
(74) *Attorney, Agent, or Firm* — Quarles & Brady LLP (57) ABSTRACT

An extract obtained from *Saxifraga* sp., *Astrantia major*, or a combination thereof and a method of treating or relieving an inflammatory-skin related condition in a subject is provided. The method comprises administering or applying a composition comprising an effective amount of an extract from *Saxifraga* sp., *Astrantia major* or a combination thereof, and a carrier, wherein the effective amount of the extract inhibits tumor necrosis factor alpha and Interleukine-1beta activity. The inflammation may be inflammation of the skin and the composition may be a skin preparation for external use.

12 Claims, 3 Drawing Sheets

(51) Int. Cl.
- *A61K 8/9789* (2017.01)
- *A61P 17/02* (2006.01)
- *A61K 9/06* (2006.01)
- *A61K 36/23* (2006.01)

(52) U.S. Cl.
CPC ............ *A61K 36/23* (2013.01); *A61P 17/02* (2018.01); *A61Q 19/08* (2013.01); *A61K 2236/331* (2013.01); *A61K 2236/333* (2013.01)

(56) References Cited

FOREIGN PATENT DOCUMENTS

| | | |
|---|---|---|
| JP | H09136823 | 5/1997 |
| WO | 2002047706 | 6/2002 |
| WO | 2007128558 | 11/2007 |
| WO | 2012135337 | 10/2012 |

OTHER PUBLICATIONS

Farage M.A. et al., "Characteristics of the aging skin." 2013, Adv Wound Care 2:5-10.

International Preliminary Report on Patentability for application PCT/IB2017/052579, dated Sep. 7, 2018, 20 pages.

International Search Report and Written Opinion for application PCT/IB2017/052579, dated Aug. 21, 2017, 15 pages.

Shin, H., et al. Anti-inflammatory effect of chlorogenic acid on the IL-8 productio in Caco-2 cells and the dextran sulphate sodium-induced colitis symptoms in C57BL/6 mice. Food Chemistry vol. 168, 2015, pp. 167-175.

Vercammen D, et. al., "Inhibition of caspases increases the sensitivity of L929 cells to necrosis mediated by tumor necrosis factor." 1998, J. Exp Med. 187:1477-1485.

Wangchuck, Phurpa, et al. Inhibition of TNF-a production in LPS-activated THP-1 monocytic cells by the crude extracts of seven Bhutanese medicinal plants. Journal of Ethnopharmacology, 2013, 148(3), 1013-1017.

Yoon, M. et al, Anti-oxidant and anti-aging activity on saxifraga stolonifera MEERBURGH Ethanol Extract. J of Pharmaceutical Society of Korea, vol. 51: 5, Oct. 2007, pp. 343-349. [abstract only].

\* cited by examiner

SAXIFRAGA EXTRACTS FOR COSMETIC OR THERAPEUTIC USE ON THE SKIN

FIELD OF INVENTION

This invention relates to extracts obtained from *Saxifraga*, and uses thereof.

BACKGROUND OF THE INVENTION

*Saxifraga* are perennial herbaceous alpine plants. The species grows in central and southern Europe in the Iberian Peninsula, the Alps and the Balkans.

Bastian et al. 2009 (Revue Suisse Vitic. Arboric. Hortic. (2009), 41 (6), 363-367) evaluated the changes in the concentration of active compounds in the aerial parts of *Saxifraga rotundifolia* plants depending on their origin, and at defining the optimum phenological stage of harvest based on the contents of phenylpropenoic acids, flavonols and flavonoid glycosides. Bastian et al. determined that in full bloom, the concentration of chlorogenic acid (0.1% of the dry matter, DM), of quercitrin (0.4% DM) and of rhamnosid luteolin (0.02% DM) was highest and that the content of myricitrin (1.3% DM) reached its maximum at seeds formation, with a relatively small variation from the stage of full bloom.

US 2015/0050316 teaches oil soluble and hydro-ethanolic extracts from *Saxifraga oppositifolia*, *Soldanella alpina* and optionally *Chlamydomonas* sp, and their use in cosmetic or dermatological preparations.

Inflammation involves the activation of the immune system in response to harmful stimuli, such as, e.g., a pathogen, infection, irritant, or damage to cells. Local immune system activation begins when damaged cells secrete signals that recruit immune system cells to the area, for example macrophages. Macrophages release pro-inflammatory cytokines, for example, interleukin-1 beta ("IL-1β") and tumor necrosis factor alpha ("TNFα" or "TNF-alpha").

Acute inflammation is an initial protective response of the body to remove an injurious stimulus by maintaining tissue integrity and contributing to tissue repair. Severe or prolonged noxious stimulation may result in a chronic inflammatory response that leads to a progressive shift in the type of cells present at the site of tissue injury. Chronic inflammation may be characterized as the simultaneous destruction and healing of tissue from the inflammatory process, with the net result of provoking injury rather than mediating repair.

There is a need for botanical and plant-derived compounds and extracts for use in applications to the skin that are non-irritating and useful in relieving an inflammatory-related skin condition, for example, anti-aging, anti-redness, or a combination thereof.

SUMMARY OF THE INVENTION

This invention relates to extracts obtained from *Saxifraga* sp., from *Astrantia major*, or a combination thereof, and uses thereof. Furthermore, this invention provides extracts obtained from one or more than one of *Saxifraga rotundifolia*, *Chrysosplenium alternifolium*, *Saxifraga androsacea*, *Saxifraga asjera*, *Saxifraga biflora*, *Saxifraga bryoides*, *Saxifraga caesia*, *Saxifraga exarata*, *Saxifraga muscoides*, *Saxifraga oppositifolia*, *Saxifraga stellaris*, *Saxifraga seguieri*, *Saxifraga paniculata*, *Saxifraga cuneifolia*, *Saxifraga aizoides*, *Saxifraga stolonifera*, from *Astrantia major*, and a combination thereof, and uses thereof.

Described herein is a method to provide relief of an inflammatory-related skin condition, by administering a composition comprising an extract from obtained from one or more than one of *Saxifraga rotundifolia*, *Chrysosplenium alternifolium*, *Saxifraga androsacea*, *Saxifraga asjera*, *Saxifraga biflora*, *Saxifraga bryoides*, *Saxifraga caesia*, *Saxifraga exarata*, *Saxifraga muscoides*, *Saxifraga oppositifolia*, *Saxifraga stellaris*, *Saxifraga seguieri*, *Saxifraga paniculata*, *Saxifraga cuneifolia*, *Saxifraga aizoides*, *Saxifraga stolonifera*, from *Astrantia major*, and a combination thereof, to the skin or related tissues, wherein the extract inhibits or modulates tumor necrosis factor (TNF) alpha activity. The extract is characterized with the property that the extract does not inhibit TNF-alpha production or TNF-alpha synthesis. The inflammatory-related skin condition may include one or more of bites or stings, skin rash, itching of the skin, blistering of the skin, sunburn, burning of the skin, UV exposure or radiation, aging of the skin, sunspot, skin allergies, hair loss, and exposure to a chemical irritant.

Furthermore, in the method of providing relief of an inflammatory-related skin condition as defined above, the composition may comprise an extract from one or more than one of *Saxifraga rotundifolia*, *Chrysosplenium alternifolium*, *Saxifraga androsacea*, *Saxifraga asjera*, *Saxifraga biflora*, *Saxifraga bryoides*, *Saxifraga caesia*, *Saxifraga exarata*, *Saxifraga muscoides*, *Saxifraga oppositifolia*, *Saxifraga stellaris*, *Saxifraga seguieri*, *Saxifraga paniculata*, *Saxifraga cuneifolia*, *Saxifraga aizoides*, *Saxifraga stolonifera*, from *Astrantia major*, and a combination thereof.

The inflammatory-related skin condition may be selected from, or arise from, a bite, a sting, a skin rash, itching of the skin, blistering of the skin, sunburn, sunspot, burning of the skin, UV exposure or radiation, aging of the skin, reducing redness of the skin, reducing a decrease in skin firmness, a skin allergy, age related spots, atopic skin, psoriasis, atopic dermatitis, hair loss, exposure of the skin to a chemical irritant, exposure of the skin to a pollutant, exposure of the skin to dirt, exposure of the skin to debris, and a combination thereof.

The TNF-alpha activity may be monitored using an in vitro assay measuring a concentration dependent inhibition of TNF-alpha-induced IL-6 release from human epithelial cells.

The TNF-alpha activity may be monitored using an in vitro assay measuring dose-dependent cytotoxity of TNF-alpha on a TNF-alpha sensitive cell line in the presence of Actinomycin D (ActD), wherein the extract inhibits cytotoxity of exogenous TNF-alpha on the cell line.

The extract may inhibit cytotoxity of TNF-alpha at a TNF-alpha concentration of greater than 1000 ng/ml of TNF-alpha. The extract may inhibit cytotoxity of TNF-alpha at a TNF-alpha concentration from about 0.01 ng/ml to about 1000 ng/ml of TNF-alpha.

In another aspect, the present invention relates to a method of inhibiting an IL-1 beta induced cellular response by administering a composition comprising an extract from *Saxifraga* sp., for example, one or more than one of *Saxifraga rotundifolia*, *Chrysosplenium alternifolium*, *Saxifraga androsacea*, *Saxifraga asjera*, *Saxifraga biflora*, *Saxifraga bryoides*, *Saxifraga caesia*, *Saxifraga exarata*, *Saxifraga muscoides*, *Saxifraga oppositifolia*, *Saxifraga stellaris*, *Saxifraga seguieri*, *Saxifraga paniculata*, *Saxifraga cuneifolia*, *Saxifraga aizoides*, *Saxifraga stolonifera*, from *Astrantia major*, and a combination thereof. The extract may be a water extract or an alcohol/water extract.

The IL-1 beta induced cellular response may result from, a bite, a sting, a skin rash, itching of the skin, blistering of the skin, sunburn, sunspot, burning of the skin, UV exposure or radiation, aging of the skin, reducing redness of the skin, reducing a decrease in skin firmness, a skin allergy, age related spots, atopic skin, psoriasis, atopic dermatitis, hair loss, exposure of the skin to a chemical irritant, exposure of the skin to a pollutant, exposure of the skin to dirt, exposure of the skin to debris, and a combination thereof.

A method of treating or relieving a skin condition is also provided. The method comprising, administering a composition comprising an effective amount of an extract obtained from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof, and a carrier, wherein the effective amount of the extract inhibits tumor necrosis factor (TNF)-alpha activity, the skin condition resulting from, a bite, a sting, a skin rash, itching of the skin, blistering of the skin, sunburn, sunspot, burning of the skin, UV exposure or radiation, aging of the skin, reducing redness of the skin, reducing a decrease in skin firmness, a skin allergy, age related spots, atopic skin, psoriasis, atopic dermatitis, hair loss, exposure of the skin to a chemical irritant, exposure of the skin to a pollutant, exposure of the skin to dirt, exposure of the skin to debris, and a combination thereof. The composition may be applied to the skin within a cream formulation, a spray, a liquid rub, a shampoo, a patch.

The extracts described herein exhibit the ability to suppress the effect of TNF and IL1 within a cell. Furthermore, the extracts possesses significant anti-free radical activity and may be used in a variety of applications, for example, providing relief from one or more than one of bites or stings, skin rash, itching of the skin, blistering of the skin, sunburn, sunspot, burning of the skin, reddening of the skin, aging of the skin, skin allergies, hair loss and the like, reduce age-related spots, retain skin firmness, attenuate skin wrinkles and exhibit an anti-ageing effect when applied to skin.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

This invention relates to extracts obtained from *Saxifraga* sp., from *Astrantia major*, and from a combination of *Saxifraga* sp., and *Astrantia major*, and uses thereof. Furthermore, this invention provides extracts obtained from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and from a combination thereof, and uses thereof.

As described herein, there is provided an extract obtained from a *Saxifraga* sp., for example, one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof. The extract may be obtained using a water extraction process of plant material. The extract may be formulated for cosmetic applications and applied to skin and related tissues, to provide relief of an inflammatory-related skin condition. The extract may also be used to reduce aging (anti-aging), reduce redness (anti-redness), or a combination thereof in the skin and related tissues. The extract may also be used to reduce hair loss.

The present disclosure also provides a method to provide relief of an inflammatory-related skin condition, by administering a composition comprising an extract from a *Saxifraga* sp., for example, from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof, to the skin and related tissues. A method to provide relief of an inflammatory-related skin condition, delay aging of skin and related tissues, reduce redness of skin and related tissues, reduce sunspot, reduce hair loss, or a combination thereof by administering a composition comprising an extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof to the skin and related tissues is also provided. The extract may be characterized by the property that the extract inhibits TNF-alpha activity in vitro.

Without wishing to be bound by theory, the property associated with the extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof, that is useful in reducing redness of skin, reduce sunspot, reducing aging of skin, age related spots, atopic skin, psoriasis, atopic dermatitis or a combination thereof, reducing hair loss, or in providing relief of an inflammatory-related skin condition, may be a result of the extracts ability to inhibit or modulate tumor necrosis factor (TNF) alpha activity, to inhibit or modulate an anti-IL1-induced cellular response, inhibit COX1, COX2 activity, inhibit lipoxygenase activity, or a combination thereof.

The composition may be used as a cosmetic, for example, a cosmetic cream, and applied to a skin or related tissue to delay aging of the skin (anti-aging property) and related tissues, to reduce redness of the skin (anti-redness property) and related tissues, or a combination of the anti-aging and the anti-redness properties, or alleviate, or provide relief of one or more than one inflammatory-related skin condition. The composition may be formulated as a preparation to be applied to the skin, for external use. The composition may also be applied for example, as a shampoo, a spray or a cream, in order to reduce hair loss.

As used herein, the terms "comprising", "having", "including," and "containing" and grammatical variations thereof, are inclusive or open-ended and do not exclude additional, unrecited elements and/or method steps. The term "consisting essentially of" when used herein in connection with a composition, use or method, denotes that additional elements, method steps or both additional elements and method steps may be present, but that these additions do not materially affect the manner in which the recited composition, method or use functions. The term "consisting of" when used herein in connection with a composition, use or method, excludes the presence of additional elements and/or method steps.

The use of the word "a" or "an" when used herein in conjunction with the term "comprising" may mean "one," but it is also consistent with the meaning of "one or more," "at least one" and "one or more than one." Any element expressed in the singular form also encompasses its plural form. Any element expressed in the plural form also encompasses its singular form. The term "plurality" as used herein means more than one, for example, two or more, three or more, four or more, and the like. As used herein, the term "about" refers to an approximately +/−10% variation from a given value. It is to be understood that such a variation is always included in any given value provided herein, whether or not it is specifically referred to.

As used herein, the term "extract" or "plant extract" refers to a concentrated preparation of a plant material obtained by isolating or purifying desired active constituents with one or more extraction techniques. Examples of extraction techniques include, but are not limited to, solvent extraction, for example but not limited to extraction using water, ethanol, methanol, a water/ethanol mixture, a water/methanol mixture, ethyl acetate, chromatography and the like.

The plant extract described herein are derived from *Saxifraga* sp., for example, one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof. As used herein, the term "derives from" or "derived from" refers to a product, compound or composition which is obtained from, or may be traced back, to a given definite source. The extract from *Saxifraga* sp., for example, one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof, may comprise one or more than one TNF-alpha inhibitor or one or more than one TNF-alpha antagonist, that is, the extract may comprise a compound or a combination of compounds that exhibit the property of inhibiting TNF-alpha activity as described herein.

"*Saxifraga rotundifolia*" (or "*S. rotundifolia*"), *Chrysosplenium altemifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera* and *Astrantia major* refer to plants which commonly grows in central and southern Europe in the Iberian Peninsula, the Alps and the Balkans. Preferably, the leaves, stems and/or roots are used for obtaining a plant extract according to the disclosure, but other plant tissues such as flowers, fruits, tubers, corms, etc. may also be used. As one of skill would understand, the Saxifragacae family comprises three genders: *Bergenia, Saxifraga* and *Chrysosplenium*. As described herein the term "*Saxifraga* sp.," includes *Saxifraga rotundifolia, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera* and *Chrysosplenium alternifolium*.

By "inhibiting TNF-alpha activity", it is meant, the selective, full or partial inhibition of TNF-alpha-induced processes, including but not limited to TNF-induced release of factors, TNF-alpha induced apoptosis, or TNF-alpha induced cytotoxicity. Examples of a direct TNF-alpha-induced process include but are not limited to, TNF-alpha induced apoptosis, or inhibition of exogenous TNF-alpha induced cytokines release, or TNF-alpha apoptosis, or inhibition of TNF-alpha induced cytotoxicity. As would be evident by one of skill in the art, alternate assays may also be used to determine direct TNF-alpha-induced process.

The TNF-alpha activity may for example be measured by an in vitro assay measuring a concentration-dependent inhibition of TNF-alpha-induced IL-6 release from human epithelial cells.

As human epithelial cells have TNF and IL1 receptors on their membrane surfaces, the exogenous addition of TNF or IL1 provokes a measurable biological reaction in these cells that is proportional to the quantity of these added compounds. The effectiveness of extracts described herein may be evaluated by determining the inhibition of this biological response and quantifying their effectiveness.

The TNF-alpha activity may for example be measured by an in vitro assay measuring dose-dependent cytotoxicity of TNF-alpha on a TNF-alpha sensitive cell line in the presence of Actinomycin D (ActD), wherein the extract inhibits cytotoxity of exogenous TNF-alpha on the cell line (for example using the method described in Vercammen D, et. al., 1998, J. Exp Med. 187:1477-1485). However, other in vitro or in vivo assays may be used to determine a TNF-alpha-induced process, as would be evident by one of skill in the art.

By TNF-alpha inhibitor (or agonist), also referred to as tumor necrosis factor alpha inhibitor (or agonist), tumor necrosis factor α inhibitor (or agonist), TNFα inhibitor (or agonist), it is meant a compound or composition that blocks, inhibits, prevents, suppresses or weakens the physiologic response to TNF-alpha. The inhibitor may block or reduce the activity of TNF-alpha either directly or indirectly. The TNF-alpha inhibitor may slow, interfere, partially block, or block TNF-alpha response. As used herein a TNF-alpha inhibitor or TNF-alpha antagonist, does not block or modify the synthesis or production of TNF-alpha in a cell. The extract described herein blocks TNF-alpha activity.

The methods described herein include, administration of an extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major*, and a combination thereof, or a composition comprising an extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major*, and a combination thereof, to the subject in need of obtaining relief of an inflammatory-related skin condition, reduce sunspot, delaying aging (anti-aging) of skin and related tissues, reducing redness (anti-redness) of skin and related tissues, or a combination thereof. The reduction of skin redness, skin aging, relief from an inflammatory-related skin condition, or a combination thereof, may be a result of anti-inflammatory activity observed with the extract in vitro. The composition therefore comprises an effective amount of an extract from one or more than one of *Saxifraga rotundifolia, Chrysosplenium altemifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major*, and a combination thereof, along with a suitable carrier or cosmetically acceptable vehicle, the effective amount of the extract characterized by inhibiting tumor necrosis factor (TNF) alpha activity.

As used herein, the "anti-inflammatory activity" or "modulating inflammation" refers to the property of a substance or composition in reducing acute and/or chronic inflammatory responses, and/or in preventing or treating an inflammatory-related condition, preferably a skin-related condition, for example an inflammatory-related skin condition. Non-limiting examples of an inflammatory-related skin condition that may be relieved using the composition described herein include one or more than one of bites or stings, skin rash, itching of the skin, blistering of the skin, sunburn, sunspot, burning of the skin, UV exposure or radiation, aging of the skin, skin allergies, age related spots, atopic skin, psoriasis, atopic dermatitis, hair loss, and exposure to a chemical irritant, pollutants, dirt or debris.

Skin aging is an example of a condition arising as a result of chronic inflammation and can be measured using known criteria (e.g. Farage M. A. et al., 2013, Adv Wound Care 2:5-10, which is incorporated herein by reference). Skin aging may be determined for example using changes in biochemical markers associated with skin condition; structural assessments of skin for example skin thickness, collagen and elastin content and turnover, collagenase and elastase production, cell size, change in shape of keratinocytes (becoming shorter and fatter) and/or corneocytes (become bigger as a result of decreased epidermal turnover), reduction of skin lipid content, changes in amino acid content, flattening of the dermo-epidermal junction, functional assessments of skin, including elasticity, torsion extensibility, neuroperception, transepidermal water loss (TEWL), and skin proliferation rate. Skin redness may be determined using a qualitative measurement of the sin, or using biochemical markers associated with skin coloration.

Certain solar rays, in particular UV A and B, cold, mechanical irritation and pollution are all factors causing an acute reaction in the skin resulting in the appearance of redness and swelling associated with a sensation of pain. This is the inflammatory response. These aggressions, even of low intensity, directly cause the release of TNF and ILL in particular by the keratinocytes of the epidermis. TNF is an extremely powerful factor that, although a beneficial physiological alert signal, can become a factor directly responsible for damages leading to the premature and accelerated ageing of the skin. TNF actually causes the release of enzymes (collagenase and elastase) that efficiently degrade the fibers of the matrix of the dermis composed of collagen and elastin, which leads to the local breakdown of the latter and causes loss of skin elasticity and the appearance of wrinkles. This effect is important, particularly for elastin, which is involved in the maintenance of the skin's firmness and is a protein produced mainly during the first three years of life, then much less thereafter.

In addition to its detrimental effect on skin flexibility and on skin capacity to keep intact dermal structural proteins, the sun has also a direct effect on the formation of sunspots (also termed lentigo). These age-related spots are caused by the repeated or too long exposure to sun and can be visible also on young people. They corresponds to melanine aggregates arising from the over production of melanocytes which react to lengthy or intense exposure to sun. Two cytokines may be involved in the stimulation of the melanine production through the effect of solar rays by melanocytes; TNF and IL1.

By relief from an inflammatory skin condition, or treating an inflammatory skin condition, it is meant, reducing the symptoms, discomfort, appearance, or a combination thereof, that are associated with the inflammation. The degree of relief or treatment may be determined by comparing one or more qualitative or quantitative factors associated with a subject that has received a composition comprising an effective amount of the extract of the present invention with the same one or more factors in a subject that has not received the composition, or that has received a composition that does not comprise an effective amount of the extract described herein. The one or more factors may be qualitative factors for example, reduced itching, reduced redness and the like, and categorized using an index, the one or more factors may be quantitative factors, for example, based on assaying a sample obtained from the subject and determining, for example, TNF-alpha activity, or the one or more factors may be a combination of qualitative and quantitative factors.

The present disclosure also provides a method of reducing the effect of a TNF-alpha initiated cytokine activity, or a IL-1β (IL-1beta) initiated cytokine activity that may be associated with an inflammatory-related skin condition, for example but not limited to skin aging, skin redness or both, by administrating an extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major*, and a combination thereof, or a composition comprising an extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major*, and a combination thereof, to a subject.

The direct activity of TNF-alpha or physiological response of TNF alpha may for example be monitored using an in vitro assay measuring a concentration-dependent inhibition of TNF-alpha-induced IL-6 release from human epithelial cells.

The direct activity of IL-1beta or physiological response of IL-1beta may for example be monitored using an in vitro assay measuring a concentration-dependent inhibition of TNF-alpha-induced IL-6 release from human epithelial cells.

Figure 1A:
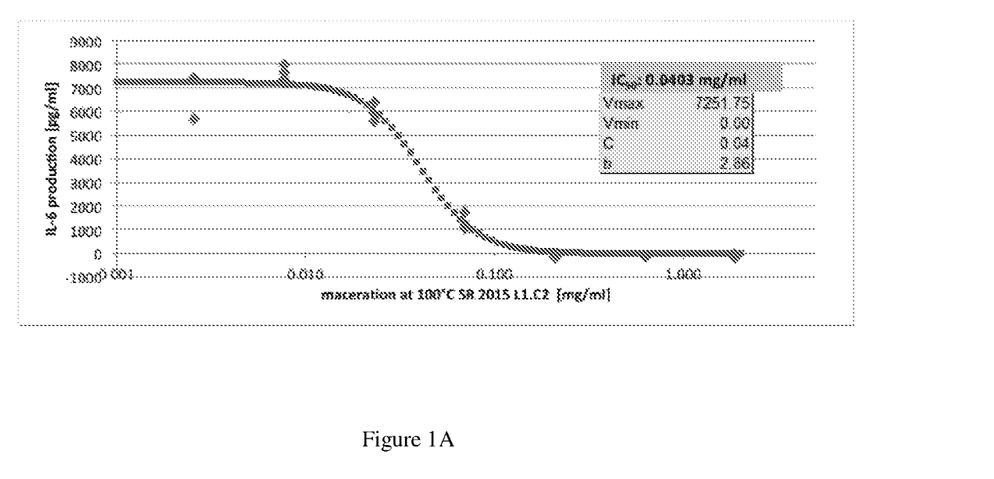
FIG. 1A shows the concentration effect of *Saxifraga rotundifolia*, on TNF alpha-induced IL-6 and IL-1 beta-induced IL-6 release from human epithelial cells.
Figure 1B:
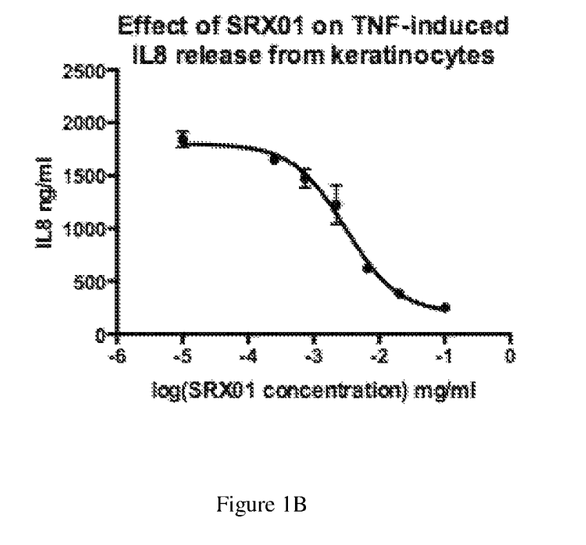
FIG. 1B shows the concentration effect of *Saxifraga rotundifolia*, on TNF alpha-induced IL-6 and IL-1 beta-induced IL-6 release from human keratinocytes. Similar results (see Table 2, Example 3) were obtained with extracts obtained from *Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, and *Astrantia major*.

For example, direct stimulation of the extract on IL-6 production by TNF-alpha or IL-1beta may be determined using human intestinal epithelial Caco-2 cells and determining the amount of IL-6 secreted in the cell medium following incubation of the cells in the plant extract, followed by the addition of TNF-alpha or IL-1beta. As shown in FIG. 1A, the *Saxifraga rotundifolia* water extract, in the presence of TNF-alpha or IL-1beta was observed to reduce IL-6 production with increasing amounts of plant extract. A similar response was observed in human kerationocytes (FIG. 1B). The anti-TNF-induced cellular response of *Saxifraga rotundifolia* water extract exhibited an IC50 of 0.0403 mg dry matter/ml. Similar results were observed (see Table 2 in Example 3) using extracts prepared from *Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Chrysosplenium alternifolium*, and *Astrantia major*, where the IC50 of the anti-TNF-induced cellular response ranged from 0.0392 mg/ml DM to 0.51 mg/ml DM. Also shown in Table 2 is the IC50 of the anti-IL-1 beta induced cellular response, which ranged from 0.0299 mg/ml DM to 0.53 mg/ml DM.

Figure 2:
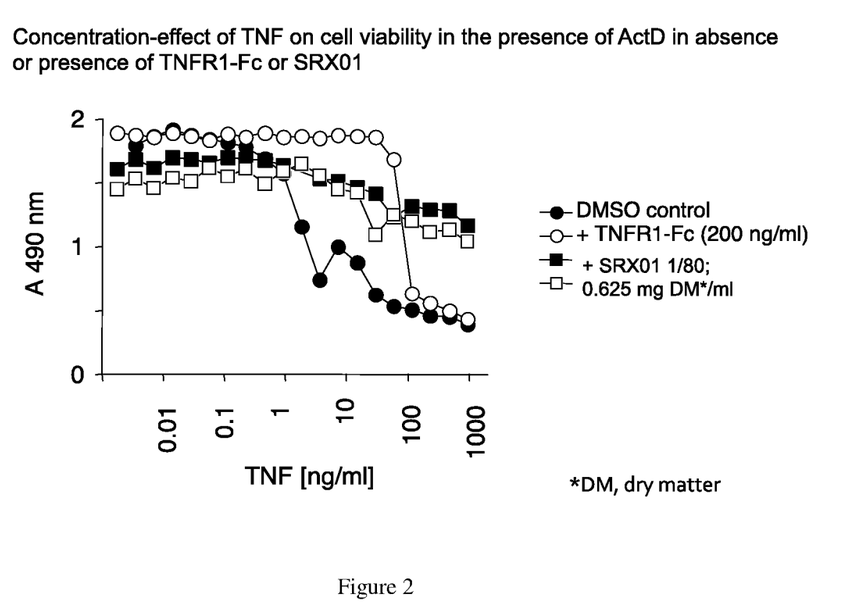
FIG. 2 shows the concentration effect of exogenous TNF-alpha on cell viability in the presence of Actinomycin D (ActD) and in the absence or presence of Tumor necrosis factor receptor 1-Fc (TNFR1-FC) or a water extract from *Saxifraga rotundifolia* (SRX01).

The activity of TNF-alpha or physiological response of TNF-alpha may for example be determined by an in vitro assay measuring dose-dependent cytotoxicity of exogenous TNF-alpha on a TNF-alpha sensitive cell line in the presence of Actinomycin D (ActD). As shown in FIG. 2 (also see Example 3), the effect of the *Saxifraga rotundifolia* extract on TNF-alpha activity results from a direct inhibition of the exogenous TNF-alpha and the effect is observed within a short period of time within minutes to hours. The effect of the extract on TNF-alpha activity may result in a partial blocking of overall TNF activity as shown in FIG. 2. The addition of an extract from *Saxifraga rotundifolia* may therefore inhibit the cytotoxity of TNF-alpha to a cell, and modulate inflammatory processes.

The extract may reduce TNF-alpha or IL-1beta activity by 30%-100%, or any amount therebetween, for example 30, 35, 40, 45, 50, 55, 60, 65, 70, 75, 80, 85, 90, 95, 100% or any amount therebetween, for example as determined using the in vitro assay described herein.

Furthermore the extract may reduce TNF-alpha/ActD-induced cell death by 30% to 100%, or any amount therebetween, for example 30, 35, 40, 45, 50, 55, 60, 65, 70, 75, 80, 85, 90, 95, 100% or any amount therebetween, for example as determined using the in vitro assay described herein.

In another aspect the disclosure relates to a method of inhibiting IL-1β induced activity that may be associated with an inflammatory-related skin condition, for example skin aging, sunspot, skin redness, age related spots, atopic skin, psoriasis, atopic dermatitis, hair loss, or a combination thereof.

The extract may have an IC50 of between 0.005 mg/ml to 2.5 mg/ml or any amount therebetween, of between 0.02 mg/ml to 2.5 mg/ml or any amount therebetween, for example 0.005 mg/ml, 0.006 mg/ml, 0.007 mg/ml, 0.008 mg/ml, 0.009 mg/ml, 0.01 mg/ml, 0.012 mg/ml, 0.015 mg/ml, 0.018 mg/ml, 0.02 mg/ml, 0.025 mg/ml, 0.03 mg/ml, 0.035 mg/ml, 0.04 mg/ml, 0.045 mg/ml, 0.05 mg/ml, 0.055 mg/ml, 0.06 mg/ml, 0.065 mg/ml, 0.07 mg/ml, 0.075 mg/ml, 0.08 mg/ml, 0.085 mg/ml, 0.09 mg/ml, 0.095 mg/ml 0.1 mg/ml, 0.15 mg/ml, 0.2 mg/ml, 0.22 mg/ml, 0.23 mg/ml, 0.24 mg/ml, 0.25 mg/ml, 0.3 mg/ml, 0.35 mg/ml, 0.4 mg/ml, 0.45 mg/ml, 0.5 mg/ml, 1.0 mg/ml, 1.5 mg/ml, 2.0 mg/ml, 2.5 mg/ml or any amount therebetween, as determined using the TNF-induced IL-6 release from human epithelial cells in vitro, or the IL-1-induced IL-6 release from human epithelial cells in vitro (as described herein), or any in vitro assays known in the art.

The extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major* and a combination thereof, may be an ethanol/water extract, or a water extract (also termed aqueous extract). For example a water extract from one or more than one of *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major* and a combination thereof, may have direct anti-TNF and anti-IL1-induced cellular response with an IC50 of between about 0.02 to about 2.5 mg dry matter/ml, or any amount therebetween.

TNF-alpha is a principal mediator of the immune and inflammatory response. As used herein, a "TNF-alpha-mediated response". TNF mediated responses may include, but are not limited to acute and chronic immune and autoimmune conditions, inflammatory conditions and the like. For example, an inflammatory-related skin condition.

One aspect of the present disclosure relates to a plant extract from one or more than one of *Saxifraga rotundifolia*,

*Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major* and a combination thereof, having an ant-inflammatory activity, for example, an inflammatory-related skin condition, wherein the extract inhibits TNF-alpha, or IL-1beta activity.

As shown with reference to FIG. 2, increasing addition of exogenous TNF-alpha, to control cells results in a significant decrease in cell viability (TNF-alpha concentrations above 1 ng/ml). The decrease in cell viability at high concentrations of TNF-alpha is also not ameliorated using an antibody specific to TNF-alpha (TNRF1-Fc). However, the addition of a plant extract from *Saxifraga rotundifolia* (SRX01) exhibits a partial protection of the cell population against TNF-alpha induced cell death over a five magnitude range of exogenous TNF-alpha concentrations. A 0-5% reduction in cell viability was observed at TNF-alpha concentrations above 1 ng/ml, with approx. 50-70% of the cell population remaining viable in the presence of up to 1000 ng/ml TNF-alpha concentrations.

These results indicate that an extract from *Saxifraga* sp., for example but not limited to, SRX01, or from *Astrantia major*, acts in a direct manner to block the TNF effect, and protect the cell against TNF-induced cell death. The protective effect of the SRX01 extract is independent of the TNF-alpha concentration. As the protective effect of SRX01 on TNF-alpha induced cell death is observed over a range of five magnitudes, from 0.01-1000 ng/ml TNF-alpha (far in excess of intracellular amounts of TNF-alpha), this effect is not a result of TNF-alpha synthesis. Furthermore, in the presence of SRX01, and in the absence of any added TNF, no TNF-induced cell death is observed.

Without wishing to be bound by theory, the protective effect of an extract from *Saxifraga* sp., for example, SRX01, or from *Astrantia major*, may be a result of modifying a TNF-alpha induced cellular response, for example, modulating a transporter that may impact the effect of TNF-alpha, modulation of a biochemical pathway, acting as an inhibitor or activator of a process involved with TNF-alpha activity, modulating gene expression (either activating or suppressing expression of genes related to TNF-alpha induced activity), or a combination thereof.

Skin (or cutaneous) comprises an epidermal layer, comprising keratinocytes, a basement membrane, and a dermal layer (comprising a papillary region and a reticular region) connected to the epidermis through the basement membrane. Related tissues of the skin may also include the hypodermis, subcutaneous tissue, and tissues of the ectoderm or mesoderm. Skin is highly reactive to environmental stimuli and the epidermal component of keratinocytes is a very rich source of both arachidonic acid and pro-inflammatory cytokines of IL-1beta and TNF-alpha. The skin dendritic cells, Langerhans cells, recognize and process antigens for further immune response of various lymphocytes and all of these cells are primarily regulated by cytokines through their specific cell surface receptors. The highly innervated skin has a high capacity for redness, swelling, and heat. In a skin system, the degree of tissue damage is frequently magnified out of proportion to the resulting inflammatory response.

Free radicals, produced when skin experiences stress, may contribute to the gradual deterioration of skin cells, and free radicals are also implicated in premature ageing. As described herein, the quantity of free radicals in sin tissue, following exposure to stress, is reduced by an extract from *Saxifraga* sp., for example, SRX01, or from *Astrantia major*, thereby slowing down the skin ageing process. For example, SRX01 exhibits an anti-free radical activity measured using the 2,2-dipenyl-1-picrylhydrazyl (DPPH) test (See Example 2). In this test, SRX01 showed a concentration-dependent antioxidant activity with an $EC_{50}$ of 0.2 mg/mL of dry matter.

Also, as described in Example 3 below, the addition of an extract from *Saxifraga* sp., for example, SRX01, or from *Astrantia major*, to an aging fibroblast cell culture model, reduced the release of collagenase and elastase into the medium. Collagenase and elastase are responsible for premature ageing of skin, in response to a stressor, for example, UV light. Furthermore in skin sample explants that were exposed to UV light, the addition of SRX01, reduced the production of these enzymes. Therefore application of an extract from *Saxifraga* sp., for example, SRX01, or from *Astrantia major*, may be effective in reducing premature aging of the skin.

Therefore the extract from *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major* and a combination thereof, may also be useful in treating inflammation of the skin, and the present disclosure provides a method for treating an inflammatory skin condition including but not limited to The inflammatory-related skin condition may include one or more of bites or stings, skin rash, itching of the skin, blistering of the skin, sunburn, sunspot, burning of the skin, UV exposure or radiation, aging of the skin, skin allergies, age related spots, atopic skin, psoriasis, atopic dermatitis, hair loss, and exposure to a chemical irritant or pollutant.

Accordingly, the composition comprising an effective amount of the extract from *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major* and a combination thereof, may be formulated as a cosmetic product comprising a suitable carrier or cosmetically acceptable vehicle. Non-limiting examples of such a product include a skin cream, a skin cleanser product, a skin toner product, a skin moisturizer product, a mask product for use on skin, a shampoo for hair treatment; a spray for skin or hair treatment. The effective amount of the extract within the composition results in inhibition of tumor necrosis factor (TNF) alpha or IL-1beta activity.

The composition comprising an effective amount of the extract from *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major* and a combination thereof, may be formulated as a product comprising a suitable carrier. Where, the effective amount of the extract within the composition results in inhibition of tumor necrosis factor (TNF) alpha activity.

Also disclosed is a method of using the composition, comprising an effective amount of the extract from *Saxi-*

*fraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Astrantia major* and a combination thereof, to treat skin, hair loss, or an inflammatory-related skin condition, in a subject in need thereof. The composition may inhibit, reduce, or both inhibit and reduce TNF-alpha activity in the skin. The compositions may further inhibiting COX1, COX2, and/or lipoxygenase activities in the skin.

Figure 3A:
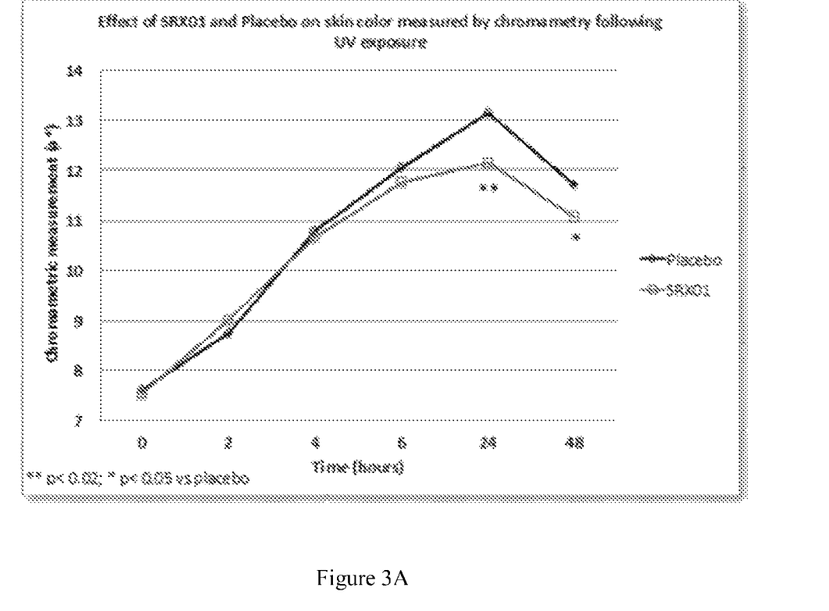
FIG. 3A shows the effect of SRX01 and a control treatment on skin color following UV light exposure for 0, 2, 4, 6, 24 and 48 hours, as measured using chromametry.
Figure 3B:
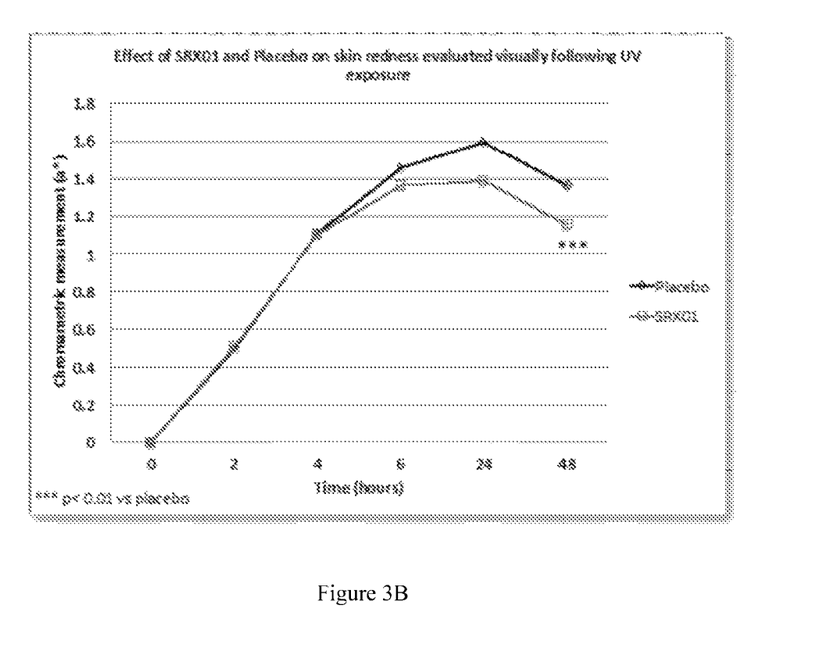
FIG. 3B shows effect of SRX01 and a control treatment on skin redness following UV light exposure for 0, 2, 4, 6, 24 and 48 hours, as measured visually.

The composition described herein may also be used to provide relief from one or more than one of bites or stings, skin rash, itching of the skin, blistering of the skin, sunburn, sunspot, burning of the skin, reddening of the skin, reducing firmness of the skin (i.e. retaining firmness of the skin), aging of the skin, skin allergies, hair loss and the like. For example, as shown in Examples 5 and 6, cream formulations comprising an extract from *Saxifraga rotundifolia* (SRX01) were observed to alleviate skin rash (Example 5; FIGS. 3A, 3B), reduce age-related spots and retain skin firmness (Example 6; Tables 3 and 4) and also exhibit a tendency towards an attenuation of wrinkles (Example 6; Table 5) thereby demonstrating the beneficial anti-ageing potential of the composition and cream formulations comprising the composition.

In one aspect there is disclosed a topical skin composition extract from a *Saxifrage* sp., for example *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major* and a combination thereof, wherein the extract is an aqueous extract from the whole plant (or any part thereof) of the *Saxifraga* sp., for example, *Saxifraga rotundifolia, Chrysosplenium altemifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major* and a combination thereof. The extract from a *Saxifraga* sp., for example, *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major* and a combination thereof, may be used to reduce TNF-alpha activity in skin cells having increased TNF-alpha activity, for example in inflamed skin.

The *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera, Saxifraga stolonifera, Astrantia major* and a combination thereof, extract described herein also exhibits antioxidant properties, and the extract may therefore be used to treat, prevent, or reduce oxidative damage to skin cells from external environmental factors, for example, pollution, sunburn, chemicals and the like. Therefore, the extracts disclosed herewith may be used to treat skin conditions associated with oxidation of skin cells.

The disclosure further relates to compositions comprising a plant extract as defined herein and/or a plant extract obtained by any of the purification methods herein; in combination with a suitable carrier, diluent or excipient.

The plants may be obtained by standard cultivation and extraction techniques known to those having ordinary skill in the art. Any suitable extraction technique known in the art may be used to prepare the plant extract having the properties described herein. In one non-limiting example, the plant (or any part of the plant such as the leaves, stems, bark, roots, fruit, flowers or flower buds, seeds, seed pods, sap, whole plant, etc.) may be disrupted by grinding of the plant and the extract may be obtained from the grinded material by accelerated solvent extraction (ASE). Other extraction processes may include, maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), and the like.

Aqueous, alcoholic, or oil based extraction techniques, or combinations thereof, may be used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the extract. Ethanol extracts, or aqueous/alcoholic extracts may be obtained using this process. The preferred extract is an aqueous extract.

The extract may then be stored in liquid form, lyophilized, or subject to further processing techniques (e.g., heating, cooling, etc.). The extract may also be formulated into a cream for topical use, for example, as described in Example 4.

The plant extracts described herein have beneficial anti-inflammatory properties and therefore, may have useful applications in the prevention and/or treatment of inflammation. Accordingly, the disclosure further contemplates methods of use, and methods of treatment, and methods to alleviate one or more inflammatory-related skin conditions, comprising the use or administration of an effective amount of a plant extract, and/or composition as defined herein. The composition comprising an effective amount of the extract from *Saxifraga* sp., or *Astrantia major*, may be formulated as a cosmetic product. Cosmetic formulations are well known in the art, for example as described in "Cosmetic Formulation of Skin Care Products" (2006, Zoe Diana Draelos, Lauren A Thaman, eds., Taylor & Francis) which is incorporated herein by reference.

A "carrier", or "cosmetically acceptable vehicle" refers to a diluent, adjuvant, excipient, with which a compound is administered. The "cosmetically acceptable" refer to additional components, inert ingredients, etc., which are suitable for use in contact with the skin tissues of humans and animals without undue toxicity, incompatibility, instability, irritation, allergic response, and the like and that may be add-mixed with the extract of the present invention. The carrier, or cosmetically acceptable vehicle may be a solvent or dispersion medium containing, for example, water, ethanol, polyol (for example, glycerol, propylene glycol, and liquid polyethylene glycol and the like), suitable mixtures thereof, and vegetable oils, water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Common moisturizing ingredients (occlusive agents) create a barrier that blocks water from escaping the skin and include petrolatum, mineral oil and dimethicone. Ingredients that attract water (humectants), for example glycerin, may also be added to lotions, as well as emollients, such as coconut oil, cetyl esters, and some silicones, to improve the feel of the composition on the skin. Emollients may reduce the tackiness and greasiness caused by the other moisturizing ingredients. Additional ingredients within the composition may include emulsifiers, for example, glyceryl stearate and stearic acid combine the oil materials with the water, thickeners fragrance, preservative, and colorants may also be included.

Prevention of the action of microorganisms in the composition may be achieved by various antibacterial and antifungal agents, for example, parabens, chlorobutanol, phenol, ascorbic acid, thimerosal, and the like. Isotonic agents, for example, sugars, sodium chloride, or polyalcohols such as mannitol and sorbitol, may also be included in the composition.

Example 1—Preparation of Extract from *Saxifraga rotundifolia*

Culture and Harvesting

*Saxifraga rotundifolia* plants are farmed above 1000 meters in the Alps under BIO Suisse label (no pesticides, insecticides or chemical fertilizer). The plants are harvested and the raw material is dried up and kept in a temperature and humidity controlled environment.

Grinding of the Plant

The entire harvested batch is homogenized by centrifugal cut with 4 mm gauze using a Retsch ZM300 at 1500 rpm. Once grinded, the material is kept in vacuum-sealed aluminum foil bags (830 mbar, welding 1.5 seconds) until extracted.

Extraction

The *Saxifraga rotundifolia* extract is obtained, for example, by accelerated solvent extraction (ASE; Dionex) from the grinded plant material using following parameters:
Cell size: 66 ml
Quantity of plant: 4 g
Quantity of support: 4 g
Solvent: H2O milliQ
Temperature: 40 or 100° C.
Heating time: 5 min
Extraction duration: 10 min
% Flush: 65
Number of cycle: 1
Following ASE, the extract may be filtered.

The *Saxifraga rotundifolia* extract may also be obtained by an extrusion process (using a helical or screw press). Both the ASE and the extrusion process may be carried out with either water as the solvent, as using an alcohol/water solvent, for example an ethanol/water solvent. Water is the preferred solvent. If an alcohol/water solvent is used, then the ratio of alcohol:water, typically ethanol:water, is 30%: 70%, for example as described in Bastian et. al 2009 (supra).

The *Saxifraga rotundifolia* extract may also be obtained by any other extraction process including maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), and the like.

An example of an extract obtained by ASE, maceration and maceration under pressure using water as the solvent is "SRX01"

The method described above was also used to prepare extracts from the following plants: *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, and *Astrantia major*.

Example 2—Characterization of Extract

Determination of the Dry Matter

A 5 ml aliquot of extract is evaporated until dryness in an oven at 105° C. The dry matter is determined by gravimetric determination in duplicate.

High-Pressure Liquid Chromatography (HPLC) Profile

The three major peaks (chlorogenic acid, myricitrin and quercitrin) are measured as follows. An aliquot of the extract is filtered through a 0.46 µm filter. The HPLC is performed on a Waters system equipped with an auto sampler, a pump and a DAD detector with an analytical cell. The run is performed on a Kinetex 5µ C18 150×4.6 mm (Phenomenex) column with a 0.8 ml/min. flow. Detection is performed at a 360 nm wavelength. Injection volume is set to 20 µl. The peak area is normalized with the dry matter of the extract.

DPPH Measurement

Seven serial dilution (dilution factor 4) are performed and a 20 µl sample of each dilution is analyzed in triplicate on a transparent microwell plate. The measurement is performed on a Berthold microplate reader at a 520 nm wavelength. 300 µl of DPPH reactive (2,2-Diphenyl-1-picrylhadrazyl, 40 mg/l in methanol) are added to the well and after 30 minutes of incubation the absorbance of the plate is measured. The inhibition curve obtained allows determining the EC50 in mg/ml of dry matter.

Several components of the extracts are listed in Table 1.

TABLE 1

Dry matter (MS), DPPH and HPLC results for various water extracts obtained from *Saxifraga rotundifolia* (SRX01).

| Extract type | MS Mg/ml | DPPH Mg/ml | Chlorogenic Acid uV * s | Myrictrin uV * s | Quercitrin uV* |
|---|---|---|---|---|---|
| SRX01 ASE 100° C. | 10.9 | 159.76 | 507764 | 2875440 | 2123908 |
| SRX01 Maceration 100° C. | 8.43 | 166.92 | 310719 | 2425280 | 1704682 |
| SRX01 Maceration under pressure | 7.98 | 157.72 | 291421 | 1443797 | 984184 |

| | Ratio Chlor/Myr | Ratio Chlor/Quer | Ratio Myr/Quer |
|---|---|---|---|
| SRX01 ASE 100° C. | 0.18 | 0.24 | 1.35 |
| SRX01 Maceration 100° C. | 0.13 | 0.18 | 1.42 |
| SRX01 Maceration under Pressure | 0.20 | 0.30 | 1.47 |

Example 3—Biological Activity of Extract

Inhibition of Tumor Necrosis Factor (TNFα) or Interleukine-1 Beta (IL-1β) Activity
IL-6 Production The activity of TNF-alpha or physiological response of TNF-alpha may for example be monitored using an in vitro assay measuring a concentration-dependent inhibition of TNF-alpha-induced IL-6 release from human epithelial (CACO2) cells (see FIG. 1A) or IL-8 release from human keratinocyes (FIG. 1B).

The effect of the extract on the direct stimulation of IL-6 production by Tumor Necrosis factor (TNF-alpha) or interleukine-1 (IL-1beta) is measured as follows. Adherent human intestinal epithelial Caco-2 cells, are incubated for 45 minutes with the extract to be tested. Subsequently, either TNF-alpha or IL-1beta is added to the cells in order to elicit a response. After 24 hours the amount of interleukine-6 (IL-6) secreted in the cell medium is measured by ELISA. This value is compared to the one obtained from cells that were stimulated by TNF-alpha or IL-1beta without prior incubation with the extract, as control. Cell viability is evaluated in parallel in order to examine the cytotoxicity of the tested compounds by using the 3-(4,5-dimethylthiazol-2-yl)-2,5-diphenyltetrazolium bromide (MTT) test. Sulphoraphane is used as positive control, at a final concentration of 604 prepared in medium (containing 1% FCS).

The water extract obtained from *Saxifraga rotundifolia*, was observed to have direct anti-TNF-induced cellular response with an $IC_{50}$ of 0.0403 mg dry matter/ml (see FIG. 1A). Similarly, SRX01 showed an $IC_{50}$ of 0.004 mg/mL of dry matter on the TNF-induced IL8 release in human keratinocytes in culture. This $IC_{50}$ is ten times lower than that observed in the CACO2 epithelial cells (FIG. 1A), and suggests that this extract is efficacious in this major cell population of the epidermis.

Water extracts of *Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera,* and *Astrantia major* were prepared according to the method of Example 1 and tested for inhibition of TNFα or IL-1β activity as described above. The results for the IC50 for the extracts obtained from these plants are presented in Table 2

TABLE 2

The effect of the plant extracts on the direct stimulation of IL-6 production by Tumor Necrosis factor (TNF-alpha) or interleukine-1 (IL-1beta).

|  | DM mg/ml | TNF IC50 mg/ml DM | IL-1 IC50 mg/ml DM |
|---|---|---|---|
| saxifraga stellaris | 3.36 | 0.0392 | 0.0299 |
| saxifraga rotundifolia | 4.39 | 0.0406 | 0.0392 |
| saxifraga seguieri | 1.80 | 0.0469 | 0.052 |
| saxifraga paniculata | 20.65 | 0.0496 | 0.0589 |
| saxifraga cuneifolia | 10.24 | 0.0734 | 0.0605 |
| saxifraga muscoides | 12.26 | 0.0832 | 0.0753 |
| saxifraga oppositifolia | 18.63 | 0.0854 | 0.0743 |
| saxifraga biflora | 4.27 | 0.1068 | 0.1046 |
| saxifraga aizoides | 13.11 | 0.1299 | 0.128 |
| saxifraga caesia | 24.59 | 0.1555 | 0.2166 |
| saxifraga bryoides | 849.61 | 0.2239 | 0.2154 |
| saxifraga asjera | 31.27 | 0.2293 | 0.2121 |
| saxifraga androsacea | 4.32 | 0.2704 | 0.1973 |
| saxifraga exarata | 40.12 | 0.2836 | 0.2832 |
| saxifraga stolonifera | 13.55 | 0.3046 | 0.2417 |
| chrisosplenium alternifolium | 129.24 | 0.3486 | 0.293 |
| Astrantia major | 9.99 | 0.51 | 0.53 |

DM: Dry matter.

The inhibition of TNF-alpha activity is also determined using an in vitro assay that measures the dose-dependent cytotoxity of exogenous TNF-alpha within a TNF-alpha-sensitive cell line in the presence of Actinomycin D (ActD; see FIG. 2) for a period of 24 hours. The cells were incubated in DMSO (control), in the presence of a TNFR1-Fc antibody [ref], or in the presence of the extract (SRX01) produced according to the method of Example 1, and cell viability determined at 490 nm.

In the presence of DMSO, and absence of exogenous TNF-alpha, the cells were viable over the duration of the assay. With increasing addition of exogenous TNF-alpha, to the DMSO-treated cells, a marked decrease in cell viability is observed at TNF-alpha concentrations above 1 ng/ml. The addition of an antibody specific to TNF-alpha, TNRF1-Fc, maintained cell viability to approximately 100 ng/ml exogenous TNF-alpha, and then cell viability decreased dramatically with increased TNF-alpha concentrations. Without wishing to be bound by theory, after a certain concentration of TNF-alpha, the TNRF1-Fc antibody may become saturated and unavailable to bind additional TNF-alpha.

Of interest, is that addition of SRX01 partially protected the cells against TNF-alpha induced cell death over the wide range of exogenous TNF-alpha concentrations. While a slight reduction in cell viability was observed at TNF-alpha concentrations above 1 ng/ml, approx. 50-70% of the cell population remained viable even when incubated at very high TNF alpha concentrations of 1000 ng/ml. This results indicates that SRX01 is able to provide partial protection to these cells in the presence of high concentrations of TNF-alpha.

The protective effect of SRX01 on TNF-alpha induced cell death is observed in the presence of very high concentrations of exogenous TNF-alpha (and over a range of five magnitudes; from 0.01-1000 ng/ml TNF-alpha), and at concentrations that are far in excess of that of any internal TNF-alpha that may be produced intracellularly as a result of the various treatments. Therefore, the protective effect of the SRX01 extract is not a result of TNF-alpha synthesis.

The effect of the *Saxifraga rotundifolia* extract on TNF-alpha activity results from an inhibition or modulation of the effect of exogenous TNF-alpha, and the effect is observed within a short period of time (hours), which is suggestive of an direct response. This inhibition is not a result of modifying the synthesis or production of TNF-alpha.

The addition of an extract from *Saxifraga rotundifolia* may therefore be used to inhibit the cytotoxic effect of exogenous TNF-alpha on a cell, for example, modulating an inflammatory response.

The effect of the extract on TNF-alpha activity is resulting from a direct inhibition/blocking of the effect of an exogenous application of TNF and does not appear to be a result of modifying the synthesis or production of TNF-alpha. Furthermore, the effect of the water extract also referred to as "SRX01" on TNF-alpha activity may result in a partial blocking of overall TNF activity as seen in FIGS. 1A and 1B.

Effect of SRX01 on Collagenase and Elastase

In order to study whether the anti-TNF effects of SRX01 could exhibit inhibitory effects on the release of collagenase and elastase, which are responsible for premature ageing of skin, in response to a stressor, UV light, two models were analyzed, aged human fibroblasts and skin explants that were exposed to UV light.

Human fibroblasts in culture that replicate a large number of times progressively present a phenotype characteristic of senescence (Hayflick model) with a significant increase in the secretion of matrix metalloproteinase 1 (MMP-1; also known as interstitial collagenase). MMP-1 is responsible for the degradation of collagen fibers in the matrix of the dermis. The fibroblasts used in this test were aged (17 replications) and the levels of MMP-1 compared. The aged control fibroblasts secreted approx. four times more MMP-1 than younger control fibroblasts. Addition of SRX01 at a concentration of 0.02 mg/mL of dry matter inhibited approx. 40% of the secretion of MMP-1 by aged fibroblasts. These results therefore demonstrate a beneficial inhibitory effect of SRX01 on the production of an enzyme, MMP-1, that attacks the structure of the skin.

In order to demonstrate that the effects observed in cell culture could be replicated in intact tissue. The effect of SRX01 on the release of elastase and collagenase from skin explants kept alive for 24 hours, and subject to UV exposure, were tested. The skin explants were obtained from patient's following plastic surgery. Depending on the sensitivity of the donor's skin exposure to UV, the treatment of the sin explants caused a significant release of these two enzymes through a cascade implying the effects of TNF produced in the epidermis. SRX01 at the concentration of 2.658 mg/mL of dry matter suppressed 93.5% of the production of MMP-1 and 67.2% of the production of elastase in a statistically significant manner. Effects were also observed at lower concentrations but with higher variability (which may be a result in the various skin explants tested since some explants exhibited no response to UV stimulation).

Example 4: Formulation of the Extract

An extract obtained from a *Saxifraga* sp., for example, *Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga stolonifera*, from *Astrantia major*, and a combination thereof, using the method described in Example 1 may be formulated within a cosmetically acceptable cream, shampoo, or spray as would be known to one of skill in the art, for example but not limited to "Cosmetic Formulation of Skin Care Products" (2006, Zoe Diana Draelos, Lauren A Thaman, eds., Taylor & Francis; which is incorporated herein by reference).

In order to study the potential of SRX01 as active ingredient in cosmetics and to be able to test its clinical effectiveness in humans, it was incorporated into different cosmetics formulas. Several pharmaceutical forms (gel-cream, emulsion) incorporating the extract were developed. No instability of the formulations or major organoleptic changes in the model-formulas tested were observed.

SRX01 was formulated at 5% (w/w) in a simple emulsion formula. The concentration of SRX01 of 5% (w/w) was determined following the toxicology study carried out at 0.4 mg/mL of dry matter in the Keratinosens test (OECD guide line N°442D, February, $4_{th}$, 2015: In vitro Ski Sensitisation: ARE-Nrf2 Luciferase Test Method). This concentration permitted daily repeated applications and cumulative uses of creams containing SRX01. The cream fabricated in this way was stable and cleared the Challenge Test (compliant with criterion A at 28 days according to the ISO 11930) and the skin tolerance test (non-irritant Patch Test). Single application of 0.02 ml of the test sample was placed on the external surface of the arm, and maintained for 48 hours in contact with the skin, with the help of an occlusive patch; (Finn Chamber).

Example 5: Reduction of Skin Rash

A randomized, single-blind clinical study of the effect of SRX01 on actinic rash caused by exposure to UV in 23 female volunteers aged 18 to 60 years with sensitive skin was carried out. The study assessed the effect of a cream containing 5% (0.4 mg/mL of dry matter) of SRX01 applied to a skin area following a UV light treatment, against a cream with an identical composition but without the active compound (placebo) that was applied to a different skin area following the UV light treatment. The UV light treatments were of the same duration, and sufficient to induce erythema.

Exposure of the skin treatment areas to UV light resulted in a rash developing. Cream treatments were applied to the appropriate skin areas 2, 4, 6, and 24 hours following exposure to UVs. The development and the intensity of the rash was measured by chromametry (chromametric measurements were made using a chromameter CR400 KONICA MINOLTA; see FIG. 3A) and also visually assessed by a trained technician (FIG. 3B), before the first application, then at 2, 4, 6, 24, and 48 hours after exposure.

As shown in FIG. 3B, chromametric measurements show an effect of the cream containing 5% SRX01 when compared with the placebo cream that becomes visible 6 hours after exposure to UVs and is statistically significant 24 and 48 hours after exposure to UVs. The visual assessment (FIG. 3B) gave a similar result with a reduction of the intensity of the observed rash with the cream containing SRX01 appearing 6 hours after exposure to UVs and becoming statistically significant 48 hours after exposure to UVs.

These results demonstrate that the SRX01 extract reduces skin rash development with a statistically significant difference observed 24 and 48 hours after treatment. In addition to considering the use of the extract for actinic or mechanical rashes, this confirms the penetration of the active ingredient in the epidermis, and demonstrates a real inhibitory power on the effects of skin insults leading to an exaggerated inflammatory response. This effect should translate effectively in a slowing down of the accelerated ageing induced by all these kind of skin insults.

The properties outlined above, suggests that, the cream formulation comprising SRX01 effectively prevents accelerated ageing, and wrinkle formation of skin, induced by repeated long term exposure to sun, cold, pollution and mechanical irritation.

Example 6: Anti-Aging Effect of SRX01

A three months, double blind, placebo controlled clinical trial on 34 female panelists aged from 50 to 70 years was carried out to determine the effect of SRX01 on eye-contour wrinkles, age-related spots and skin firmness. Instrumental measurements were obtained before (DO), and after 1

(D28), 2 (D36) and 3 (D56) months of applying the cream with SRX01 on one half of the face and neck or the same cream devoid of SRX01 (placebo/control) on the other half of the face and neck. The placebo/control cream contained moisturizing ingredients (glycerin, fatty acids) known to have moistening and skin-protecting effects.

Instrumental measurements of skin firmness used a fringe projection technique associated to a calibrated air blast (Dynaskin-4D™). Volume, area and maximal depth of the skin deformation were measured before and after repeated applications of the cream product or the placebo/control cream. The effects on the age-related spots were evaluated by chromametry using a Konica-Minolta CM-700d spectrophotometer on a pigmented spot and an adjacent spotless area of the skin on each side of the face exposed to the cream with SRX01 or the placebo/control cream. Light variable L*, individual typological angle ITA°, and chromacity coordinate b* were assessed.

The total number of wrinkles, total surface with wrinkles ($mm^2$), total length of the wrinkles (mm) and mean depth ($\mu m$) of the eye contour were measured by taking cutaneous replicae of the right and left eye's outline (crow's feet and upper part of the malar bone of both half-faces) with a silicone rubber (Silflo™, Flexico Corp.). Analysis at the completion of the trial involve creating shadows behind the crests, under a glazed light, having a known incidence angle (35°). Analysis of the grey levels is carried out (Quantirides™ Version 2.2.1.0 software with filter, Monaderm) to characterize cutaneous relief, by means of a video image analysis system.

Skin Firmness

As shown in the results presented in Table 3 below, the volume and maximal depth of the air-blast-induced skin deformation are significantly decreased on the side of the face treated with the cream containing SRX01 (crème visage ref.: 2129.04) after 1, 2 and 3 months of treatment. In addition the effect is increased on skin exposed to the cream containing SRX01 than the effects measured on the skin treated with the placebo cream (crème visage ref.: 2129.08). After one month, the volume and the maximal depth measured on the skin exposed to SRX01 was significantly better than the effects measured on the skin exposed to the placebo/control cream.

These results demonstrate that, after one month of treatment, a cream formulation comprising SRX01 significantly improved two out of the three parameters of skin firmness compared to the placebo/control cream.

Age-Related Skin Spots:

A significant change of all the indicators linked to the color of the skin spots, reflecting a decrease of pigmentation, was observed over time with application of the cream containing SRX01 (crème visage ref.: 2129.04; Table 4). No effect was observed over time in skin treated with the placebo/control cream (crème visage ref.: 2129.08). This effect is observed with reference to the chromacity coordinate b*, with a significant change observed in skin treated with the cream formulation comprising SRX01 when compared to the placebo/control cream, across all time points. Additionally, with reference to the individual typological angle (ITA) results, an increase up to +23% is observed after 3 months. The ITA increase is observed compared to the placebo/control cream at D28, and the ITA increase is significantly different at D56.

TABLE 3

Effect of cream formulation comprising SRX01 on skin firmness. Cream formulation comprising SRX01 (crème visage ref.: 2129.04); placebo/control cream formulation (crème visage ref.: 2129.08). Measurements obtained after 1 (D 28), 2 D 56) and 3 (D 84) months of treatment.

| N = 34 | TIME EFFECT | | | | | |
|---|---|---|---|---|---|---|
| | CREME VISAGE (ref.: 2129.04) Significativity (Variation Percentage) | | | CREME VISAGE (ref.: 2129.08) Significativity (Variation Percentage) | | |
| Dx/Do Comparison | D 28 | D 56 | D 84 | D 28 | D 56 | D 84 |
| Volume ($mm^3$) | S (−21%) | S (−10%) | S (−12%) | S (−9%) | S (−7%) | NS (−6%) |
| Area ($mm^2$) | S (−4%) | NS (−1%) | NS (+0%) | NS (+1%) | NS (+0%) | NS (+4%) |
| Maximum depth (mm)* | S (−16%) | S (−5%) | S (−10%) | S (−9%) | S (−8%) | S (−4%) |

| N = 34 | PRODUCT EFFECT CREME VISAGE (ref.: 2129.04) versus CREME VISAGE (ref: 2129.08) Significativity (Variation Percentage) | | |
|---|---|---|---|
| Dx/Do Comparison | D 28 | D 56 | D 84 |
| Volume ($mm^3$) | S (+11%)* | NS (+3%) | NS (+6%) |
| Area ($mm^2$) | LS (+5%) | NS (−1%) | NS (+4%) |
| Maximum depth (mm)* | S (+7%)* | NS (−3%) | NS (+6%) |

*On absolute values
S: Statistically significant probability: $p < 0.05$
LS: Probability close to significativity: $0.05 \leq p < 0.10$
NS: Not significant probability: $p > 0.10$.
*In favour of the investigational product CREME VISAGE (ref.: 2129.04)

TABLE 4

Effect of cream formulation comprising SRX01 on age related skin spots

|  |  | TIME EFFECT | | | | | |
|---|---|---|---|---|---|---|---|
|  |  | CREME VISAGE (ref.: 2129.04) Significativity (Variation Percentage) | | | CREME VISAGE (ref.: 2129.08) Significativity (Variation Percentage) | | |
| N = 34 | Dx/Do Comparison | D 28 | D 56 | D 84 | D 28 | D 56 | D 84 |
| Pigmented Spot | Light variable L* | S (+2%) | S (+2%) | S (+3%) | NS (+1%) | NS (+0%) | S (+2%) |
|  | Chromaticity coordinate b* | S (−3%) | S (−4%) | S (−6%) | NS (+1%) | NS (−1%) | S (−3%) |
|  | Individual Typological Angle I.T.A.* | S (+15%) | S (+17%) | S (+23%) | NS (+5%) | NS (+2%) | S (+14%) |
| Spotless area | Light variable L* | S (+1%) | S (+1%) | S (+1%) | S (+1%) | S (+1%) | S (+1%) |
|  | Chromaticity coordonate b* | S (−4%) | S (−6%) | S (−7%) | S (−3%) | S (−5%) | S (−6%) |
|  | Individual Typological Angle I.T.A.* | S (+7%) | S (+10%) | S (+11%) | S (+7%) | S (+8%) | S (+10%) |
| ˆ (spotless area)* | Light variable L* | NS (−10%) | NS (−10%) | NS (−14%) | NS (+1%) | NS (+15%) | NS (+0%) |
|  | Chromaticity coordinate b* | NS (−5%) | NS (+14%) | NS (+5%) | S (+44%) | S (+50%) | LS (+38%) |
|  | Individual Typological Angle I.T.A.* | NS (−7%) | NS (−3%) | NS (−8%) | NS (+12%) | LS (+21%) | NS (+4%) |

|  |  | PRODUCT EFFECT CREME VISAGE (ref. 2129.04) versus CREME VISAGE (ref. 2129.08) Significativity (Variation Percentage) | | |
|---|---|---|---|---|
| N = 34 | Dx/Do Comparison | D 28 | D 56 | D 84 |
| Pigmented Spot | Light variable L* | NS (−1%) | S (−2%)* | NS (−1%) |
|  | Chromaticity coordinate b* | S (+4%) | S (+4%)* | S (+3%)* |
|  | Individual Typological Angle I.T.A.* | LS (−10%) | S (−15%)* | NS (−8%) |
| Spotless area | Light variable L* | NS (+0%) | NS (+0%) | NS (+0%) |
|  | Chromaticity coordinate b* | NS (+1%) | NS (+1%) | NS (+1%) |
|  | Individual Typological Angle I.T.A.* | NS (+0%) | NS (−2%) | NS (−1%) |
| Δ (spotless area)* | Light variable L* | NS (+17%) | LS (+25%) | NS (+14%) |
|  | Chromaticity coordinate b* | S (+48%)* | NS (+36%) | NS (+33%) |
|  | Individual Typological Angle I.T.A.* | LS (+19%) | LS (+24%) | NS (+12%) |

*On absolute values
S: Statistically significant probability: p < 0.05
LS: Probability close to significativity: 0.05 ≤ p < 0.10
NS: Not significant probability: p > 0.10.
*In favour of the investigational product CREME VISAGE (ref.: 2129.04

Eye contour wrinkles:
With reference to Table 5 below, results obtained measuring the total number of wrinkles, the total surface of the wrinkles, the length and depth obtained silicone imprints of the wrinkles at the different time points is provided.
Table 5: Effect of cream formulation comprising SRX01 on eye contour wrinkles. Cream formulation comprising SRX01 (crème visage ref.: 2129.04); placebo/control cream formulation (crème visage ref.: 2129.08). Measurements obtained after 1 (D28), 2 (D56) and 3 (D84) months of treatment.

|  | TIME EFFECT | | | | | |
|---|---|---|---|---|---|---|
|  | CREME VISAGE (ref: 2129.04) Significativity (Variation Percentage) | | | CREME VISAGE (ref: 2129.08) Significativity (Variation Percentage) | | |
| N = 30 to 32 | | | | | | |
| Dx/Do Comparison | D 28 | D 56 | D 84 | D 28 | D 56 | D 84 |
| Total number of wrinkles | S (−10%) | NS (−5%) | S (−10%) | NS (−7%) | NS (−5%) | NS (−8%) |
| Total surface with wrinkles (mm²) | NS (−8%) | LS (−11%) | LS (−14%) | NS (−3%) | LS (−11%) | NS (+0%) |
| Total length of the wrinkles (mm) | S (−10%) | NS (−4%) | LS (−9%) | NS (−5%) | NS (−5%) | NS (−2%) |
| Total depth (μm) | S (−11%) | S (−13%) | S (−16%) | S (−8%) | S (−12%) | S (−10%) |

-continued

| N = 30 to 32 | PRODUCT EFFECT CREME VISAGE (ref.: 2129.04) versus CREME VISAGE (ref.: 2129.08) Significativity (Variation Percentage) | | |
|---|---|---|---|
| Dx/Do Comparison | D 28 | D 56 | D 84 |
| Total number of wrinkles | NS (+3%) | NS (+0%) | NS (+2%) |
| Total surface with wrinkles (mm$^2$) | NS (+5%) | NS (+0%) | NS (+14%) |
| Total length of the wrinkles (mm) | NS (+5%) | NS (−1%) | NS (+7%) |
| Total depth (μm) | NS (+3%) | NS (+1%) | NS (+5%) |

S: Statistically significant probability: $p < 0.05$
LS: Probability close to significativity: $0.05 \leq p < 0.10$
NS: Not significant probability: $p < 0.10$.

A trend over time to an improvement several of these parameters with the cream containing SRX01 (crème visage ref.: 2129.04) may be observed. However, over the time period used for this study, these effects are not statistically significantly different from those measured with the placebo cream (crème visage ref.: 2129.08). The efficacy of SRX01 in protect the skin structure damage may result in the prevention of wrinkles formation rather than reducing the existing wrinkles.

These results on age-related spots and skin firmness and the tendency towards an attenuation of wrinkles illustrate the beneficial anti-ageing potential of SRX01 and cream formulations comprising SRX01.

In addition, cream formulation comprising SRX01 exhibit significant effects on age-related spots and skin firmness. Without wishing to be bound by theory, these effects may be attributable to the mechanism of actions described in Example 3 above with respect to SRX01.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of treating or relieving an inflammatory-related skin condition comprising: administering a composition to skin in need thereof, the composition comprising an effective amount of a water extract from *Saxifraga stellaris, S. rotundifolia, S. seguiere, S. paniculata*, or a combination thereof, and a carrier, wherein the composition is administered to the skin following exposure of the skin to a factor causing the inflammatory-related skin condition, thereby treating or relieving of the inflammatory-related skin condition, wherein the inflammatory skin condition is selected from the group consisting of bites, stings, skin rash, itching of the skin, blistering of the skin, sunburn, sunspot, burning of the skin, reducing a decrease in skin firmness, a skin allergy, age related spots, psoriasis, atopic dermatitis, hair loss, exposure of the skin to a pollutant, and a combination thereof and, wherein the effective amount of the water extract inhibits tumor necrosis factor (TNF)-alpha activity by 30-100%.

2. The method of claim 1, wherein the TNF-alpha activity is measurable by an in vitro assay measuring dose-dependent cytotoxity of TNF-alpha on a TNF-alpha sensitive cell line in the presence of Actinomycin D (ActD), wherein the extract inhibits cytotoxity of exogenous TNF-alpha on the cell line.

3. The method of claim 1, wherein the TNF-alpha activity is measurable by an in vitro assay measuring a concentration-dependent inhibition of TNF-alpha-induced IL-6 release from human epithelial (CACO$_2$) cells.

4. The method of claim 1, wherein the extract inhibits cytotoxity of TNF-alpha at an TNF-alpha concentration of greater than 1000 ng/ml of TNF-alpha.

5. The method of claim 1, wherein the extract inhibits cytotoxity of TNF-alpha at an TNF-alpha concentration from about 0.01 ng/ml to about 1000 ng/ml of TNF-alpha.

6. The method of claim 1, wherein the extract inhibits COX1, COX2, and lipoxygenase activities over a concentration range of 5.0-9 mg/ml.

7. The method of claim 1, wherein the composition is a skin preparation for external use.

8. The method of claim 2, wherein the extract comprises one or more than one phenylpropenoic acid or one or more than one flavonoid.

9. The method of claim 8, wherein the phenylpropenoic acid, or one of the phenylpropenoic acids, is a chlorogenic acid.

10. The method of claim 1, wherein the extract further induces an anti-IL1-cellular response.

11. The method of claim 1 wherein the composition further comprises a water extract of a plant selected from the group of *Astrantia major, Saxifraga rotundifolia, Chrysosplenium alternifolium, Saxifraga androsacea, Saxifraga asjera, Saxifraga biflora, Saxifraga bryoides, Saxifraga caesia, Saxifraga exarata, Saxifraga muscoides, Saxifraga oppositifolia, Saxifraga stellaris, Saxifraga seguieri, Saxifraga paniculata, Saxifraga cuneifolia, Saxifraga aizoides, Saxifraga slolonifera*, and a combination thereof.

12. The method of claim 1, wherein the TNF-alpha activity is measurable by an in vitro assay measuring a concentration-dependent production of IL-6 in human epithelial cells.

* * * * *

UNITED STATES PATENT AND TRADEMARK OFFICE
CERTIFICATE OF CORRECTION

PATENT NO. : 10,813,962 B2
APPLICATION NO. : 16/096241
DATED : October 27, 2020
INVENTOR(S) : Vincent Mutel et al.

Page 1 of 1

It is certified that error appears in the above-identified patent and that said Letters Patent is hereby corrected as shown below:

In the Specification

Column 4, Line 27, "altemifolium" should be -- alternifolium --.

Column 6, Line 23, "altemifolium" should be -- alternifolium --.

Column 7, Line 47, "altemifolium" should be -- alternifolium --.

Column 13, Line 40, "altemifolium" should be -- alternifolium --.

In the Claims

Column 26, Claim 11, Line 56, "slolonifera" should be -- stolonifera --.

Signed and Sealed this
Twenty-ninth Day of December, 2020

Andrei Iancu
*Director of the United States Patent and Trademark Office*